US00PP11827P2

(12) United States Plant Patent
Fuess

(10) Patent No.: US PP11,827 P2
(45) Date of Patent: Mar. 27, 2001

(54) CHRYSANTHEMUM PLANT NAMED 'EMPIRE CONCERTO'

(76) Inventor: Janet S. Fuess, 22 Country Club Dr., New York Mills, NY (US) 13417

( * ) Notice: Subject to any disclaimer, the term of this patent is extended or adjusted under 35 U.S.C. 154(b) by 0 days.

(21) Appl. No.: 09/225,016

(22) Filed: Jan. 4, 1999

(51) Int. Cl.[7] ..... A01H 5/00

(52) U.S. Cl. ..... Plt./291

(58) Field of Search ..... Plt./291, 287

*Primary Examiner*—Howard J. Locker
(74) *Attorney, Agent, or Firm*—C. A. Whealy

(57) ABSTRACT

A distinct cultivar of Chrysanthemum plant named 'Empire Concerto', characterized by its uniformly mounded plant habit; very uniform flowering; decorative-type inflorescences that are about 5.4 cm in diameter; attractive light pink ray florets; and numerous inflorescences per plant.

1 Drawing Sheet

BACKGROUND OF THE INVENTION

The present invention relates to a new and distinct cultivar of Chrysanthemum plant, botanically known as *Dendranthema grandifora* and referred to by the cultivar name Empire Concerto.

The new cultivar is a product of a planned breeding program conducted by the Inventor in New York Mills, N.Y. The objective of the breeding program is to create new garden-type Chrysanthemum cultivars having inflorescences with desirable inflorescence forms and floret colors and good garden performance.

The new cultivar originated from a cross made by the Inventor in October, 1993, of the *Dendranthema grandifora* cultivar Pink Champagne (U.S. Plant Pat. No. 6,920) as the female, or seed, parent with an unidentified proprietary seedling selection as the male, or pollen, parent.

The cultivar Empire Concerto was discovered and selected by the Inventor as a flowering plant within the progeny of the stated cross in a controlled environment in New York Mills, N.Y., in Sepember, 1994. The selection of this plant was based on its desirable inflorescence form and ray floret color.

Asexual reproduction of the new cultivar by terminal cuttings taken in a controlled environment in New York Mills, N.Y., has shown that the unique features of this new Chrysanthemum are stable and reproduced true to type in successive generations.

SUMMARY OF THE INVENTION

The cultivar Empire Concerto has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Concerto'. These characteristics in combination distinguish 'Empire Concerto' as a new and distinct cultivar:

1. Uniformly mounded plant habit.
2. Very uniform flowering.
3. Decorative-type inflorescences that are about 5.4 cm in diameter.
4. Attractive light pink ray florets.

5. Numerous inflorescences per plant.

The new Chrysanthemum is similar to the Chrysanthemum cultivar Debonair (disclosed in U.S. Plant Pat. No. 5,324). However in side-by-side comparisons under commercial practice, plants of the new Chrysanthemum differed from plants of the cultivar Debonair in the following characteristics:

1. Plants of the new Chrysanthemum have a more uniform growth habit than plants of the cultivar Debonair.
2. Plants of the new Chrysanthemum flower about two weeks later than plants of the cultivar Debonair.
3. Plants of the new Chrysanthemum have larger inflorescences than plants of the cultivar Debonair.
4. Plants of the new Chrysanthemum flower more uniformly than plants of the cultivar Debonair.
5. Ray florets of plants of the new Chrysanthemum are lighter in color than ray florets of plants of the cultivar Debonair.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Empire Concerto'.

The photograph at the bottom of the sheet comprises a close-up view of typical inflorescences of the cultivar 'Empire Concerto'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown without cover under natural season conditions.

Measurements and numerical values represent averages for typical flowering plants.

Botanical classification: *Dendrathema grandiflora* cultivar Empire Concerto.

Commerical classification: Decorative-type garden chrysanthemum.

Parentage:

*Female or seed parent.*—*Dendranthema grandiflora* cultivar Pink Champagne, disclosed in U.S. Plant Pat. No. 6,920.

*Male or pollen parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle. Stems initially upright, then outwardly spreading giving a uniformly mounded appearance to the plant. Freely branching with lateral branches potentially developing at every node, when pinched, about 10 laterals develop.

*Plant height.*—About 33 cm.

*Plant spread.*—About 41 cm.

*Foliage description.*—Leaf arrangement: Alternate. Length: About 6.5 cm. Width: About 4.9 cm. Apex: Mucronate. Base: Attenuate to truncate. Margin: Palmately lobed, sinuses parallel to convergent. Texture: Upper surface very pubescent; lower surface, moderately pubescent. Veins prominent on lower surface. Petiole length: About 1.8 cm. Petiole diameter: About 3 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Decorative-type inflorescence form with elongated spoon-shaped ray florets. Inflorescences borne on terminals above foliage, arising from leaf axils. Disk and ray florets arranged acropetally on a capitulum. One inflorescence per terminal with numerous inflorescences per plant, about 8 per lateral stem.

*Flowering response.*—Under natural season conditions, plants flower in late September in the Northern Hemisphere about 83 days after planting and flower for at least three weeks depending on weather conditions.

*Inflorescence bud* (*before showing color*).—Height: About 5 mm. Diameter: About 8 mm. Phyllary color: Close to 141A.

*Inflorescence size.*—Diameter: About 5.4 cm. Depth (height): About 2.1 cm. Diameter of disc: About 4 mm.

*Ray florets.*—Shape: Elongated spoon, concave. Length: About 2.6 cm. Width: About 6 mm. Apex: Dentate. Margin: Entire. Texture: Smooth, glabrous, satiny. Orientation: Initially upright, then horizontal to slightly upright, about 90 to 110° C. to the peduncle. Number of ray florets per inflorescence: Typically more than 150. Color: When opening: Creamy white, close to 11C to 11D. Opened inflorscence: Upper surface: Light pink, 65A to 65B, fading to 65C to 65D. Lower surface: Light pink, 65D to almost white.

*Disc florets.*—Shape: Tubular, apex dentate. Length: About 4 mm. Width: Apex: About 1 mm. Base: About 1 mm. Number of disc florets per inflorescence: About 12. Color: Immature: 154A. Mature: Apex: 9A. Mid-section and base: Whitish green.

*Peduncle.*—Aspect: Flexible, angled about 45° C. to the stem. Length: First peduncle: About 8.2 cm. Fourth peduncle: About 10.6 cm. Diameter: About 3 mm. Texture: Pubescent. Color: Young, 146A; Older, 187A.

*Reproductive organs.*—Androecium: Present on disc florets only. Anther color: 9A. Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Empire Concerto', as illustrated and described.

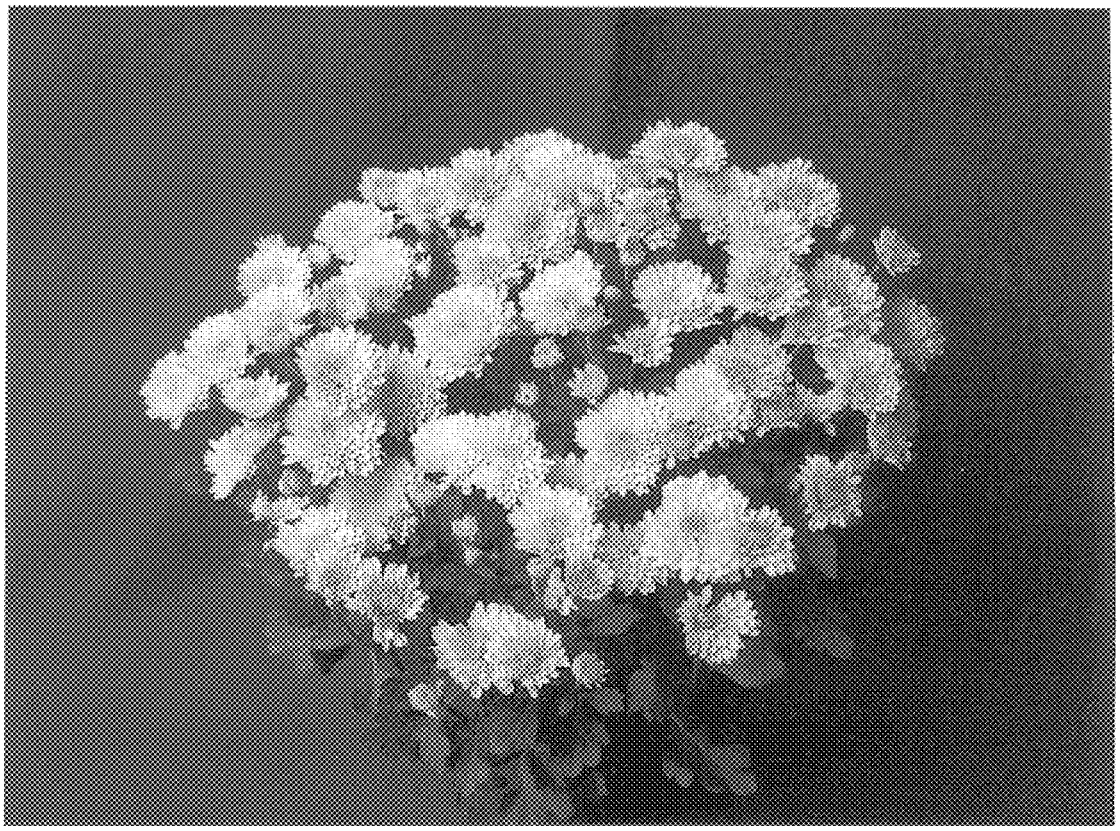
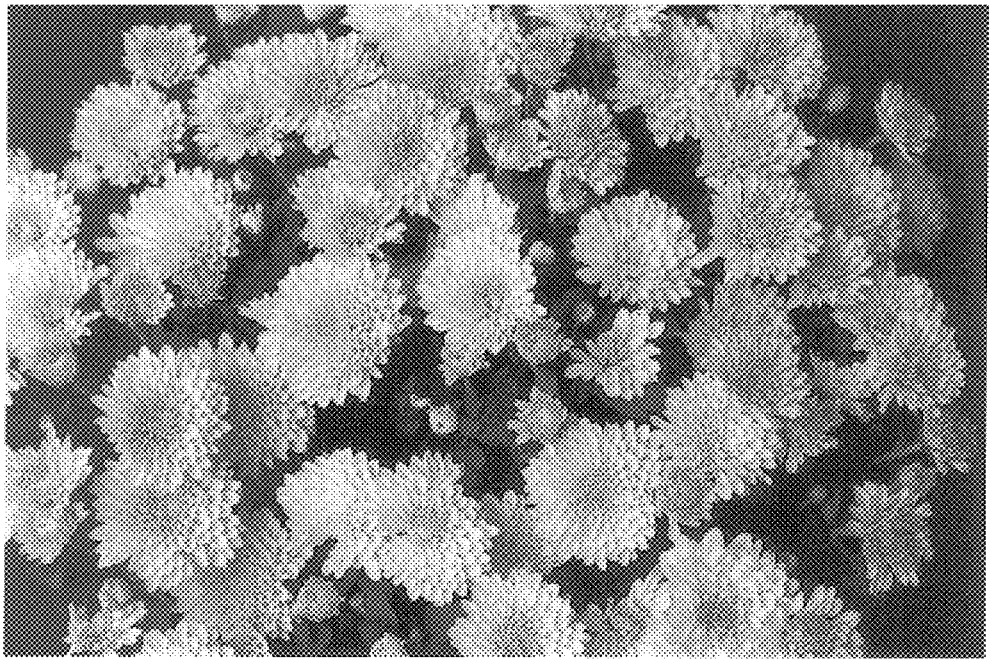

* * * * *